United States Patent [19]
Yamamoto et al.

[11] Patent Number: 5,749,865
[45] Date of Patent: May 12, 1998

[54] ABSORBENT ARTICLE OF PANTS TYPE

[75] Inventors: Masamitsu Yamamoto; Takamitsu Igaue; Toru Sasaki, all of Ehime-ken, Japan

[73] Assignee: Uni-Charm Corporation, Ehime-ken, Japan

[21] Appl. No.: 691,047

[22] Filed: Aug. 1, 1996

[30] Foreign Application Priority Data

Aug. 2, 1995 [JP] Japan .................................... 7-197732

[51] Int. Cl.⁶ ................................................ A61F 13/15
[52] U.S. Cl. ................................ 604/385.2; 604/396
[58] Field of Search ........................ 604/385.1, 385.2, 604/393–396

[56] References Cited

U.S. PATENT DOCUMENTS 5,415,649  5/1995  Watanabe et al. ............... 604/385.2
5,449,353  9/1995  Watanabe et al. ............... 604/385.2

FOREIGN PATENT DOCUMENTS 4354948  12/1992  Japan ............................... 604/394
4371147  12/1992  Japan ............................. 604/385.2
4371148  12/1992  Japan ............................. 604/385.2
7-44945   5/1995  Japan .
2253131   9/1992  United Kingdom ........... 604/385.2
9317648   9/1993  WIPO ............................. 604/394

*Primary Examiner*—Robert A. Clarke
*Assistant Examiner*—K. M. Reichle
*Attorney, Agent, or Firm*—Lowe, Price LeBlanc & Becker

[57] ABSTRACT

An absorbent pants type article has a front waist-opening marginal stretchable region and a front waist stretchable region having upper, intermediate and lower stretchable subregions. The elongation stress of the front waist-opening marginal stretchable region is greater than the corresponding stress in the lower stretchable subregion. The stress in the lower stretchable region is greater than the stress in the upper stretchable subregion which is in turn greater than the stress in the intermediate stretchable subregion.

11 Claims, 4 Drawing Sheets

5,749,865

ABSORBENT ARTICLE OF PANTS TYPE

BACKGROUND OF THE INVENTION

The present invention relates to an absorbent pants type article and, more particularly to a disposable absorbent pants type, incontinence pants, or training pants.

To improvement the fitness of a disposable diaper to a wearer's body, it is well known, for example, from Japanese Patent Application Publication No. Hei7-44945 to provide a plurality of elastic members (referred to hereinafter as auxiliary elastic members) in respective middle regions of front and rear waist regions of the diaper between a stretchable waist-opening and a pair of stretchable leg-openings.

Generally, a baby's body form is characterized by a prominent belly. Therefore, once the waist-opening upper end of the diaper placed on a baby's body has shifted downward beyond an apex of the baby's prominent belly as the baby moves, the diaper tends to further shift downward along the curve of the belly's prominence, often resulting in "slip down" of the diaper as a whole, even if it is not a complete "slip down". This "slip down" problem necessarily results in a loss of fitness and causes undesirable excretion leakage.

More specifically, in the above diaper, the auxiliary elastic members are concentratively distributed in the respective middle regions of the diaper front and rear waist regions. These middle regions provided with the auxiliary elastic members are located around the apex of the belly's prominence when the diaper is worn. Thus, it will be difficult for these auxiliary elastic members to prevent "slip down". These elastic members also tend to exert excessive pressure on the middle regions of the baby's belly which may obstruct smooth abdominal breathing.

A liquid-absorbent core panel is provided between the top- and backsheets and includes a mixture of various materials such as fluff obtained by crushing woody pulp fibers and superabsorptive polymer particles. The core panel is usually more or less compressed and therefore semi-rigid. With this semi-rigid core panel, in combination with the elastic members provided around the waist- and leg-openings, regions of the diaper extending in proximity of the leg-openings may be lifted off the baby's skin and consequently cause undesirable excretion leakage.

It has been found that the aforesaid problems can be effectively eliminated by arranging elastic members of relatively high elongation stresses in waist-opening marginal regions as well as in upper and lower subregions of the front and rear waist regions of the diaper so that elastic members arranged in intermediate subregions of the front and rear waist regions may preferably function to hold an inner surface of the diaper in these subregions in soft but gap-free contact with a baby's skin. It has also been found that elongation stresses of the auxiliary elastic members provided on the rear waist region may be lower than those of the auxiliary elastic members provided on the front waist region of the diaper because, in view of the particular body form substantially common to babies, the rear waist region is less important than the front waist region for prevention of "slip down".

The invention is based on the above-mentioned findings and aims to construct an absorbent article of pants type such as a diaper, considering the typical body form of a baby as well as functions of respective components of the articles, so that the auxiliary elastic members as well as the elongation stresses thereof may be efficiently distributed substantially over all the front and rear waist regions of the article.

SUMMARY OF THE INVENTION

The object set forth above is achieved, according to the invention, by an absorbent pants type article comprising a laminated panel composed of a liquid-permeable topsheet, a liquid-impermeable backsheet and a liquid-absorbent core panel disposed between the topsheet and the backsheet. The laminated panel is folded in two sections which are bonded together along transversely opposite side edges thereof except at a longitudinally intermediate region, to define front and rear waist regions, a crotch region, a waist-opening and a pair of leg-openings. A first elastic member extends around the waist-opening so as to be circumferentially stretchable. A second elastic member is disposed around each of the leg-openings so as to be circumferentially stretchable and a third elastic member extends transversely between the waist-opening and the leg-openings across the core panel so as to be circumferentially stretchable. The absorbent pants type article characterized in that the first elastic member is arranged in front and rear waist-opening marginal stretchable regions defined between respective upper ends of the waist-opening and respective first border lines transversely extending along respective upper ends of the core panel as viewed in the front and rear waist regions. The third elastic member provided on the front waist region is arranged in a front waist stretchable region defined between the first border line in the front waist region and a second border line connecting respective upper portions of the pair of leg-openings in the front waist region. The front waist stretchable region comprises upper, intermediate and lower stretchable subregions. The first elastic member in the front waist-opening marginal stretchable region presents an elongation stress higher than that presented by the third elastic member in each of the upper and lower stretchable subregions and the third elastic member in each of the upper and lower stretchable subregions presents an elongation stress higher than that presented by the third elastic member in the intermediate stretchable subregion.

DETAILED DESCRIPTION OF THE PREFERRED EMBODIMENT

Figure 1:
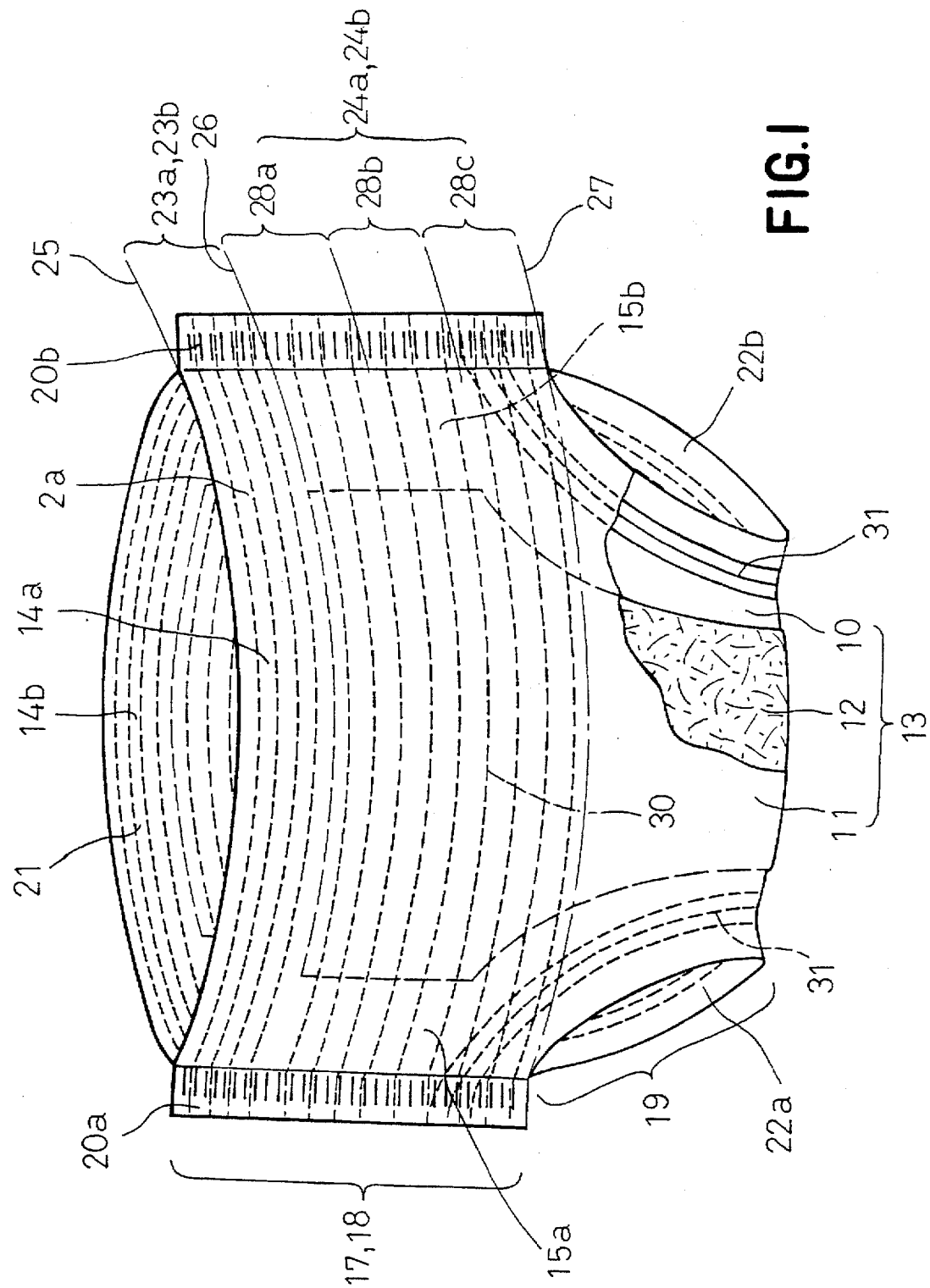
FIG. 1 is a perspective view of a disposable diaper embodying an absorbent pants type article according to the invention as partially broken away.
Figure 2:
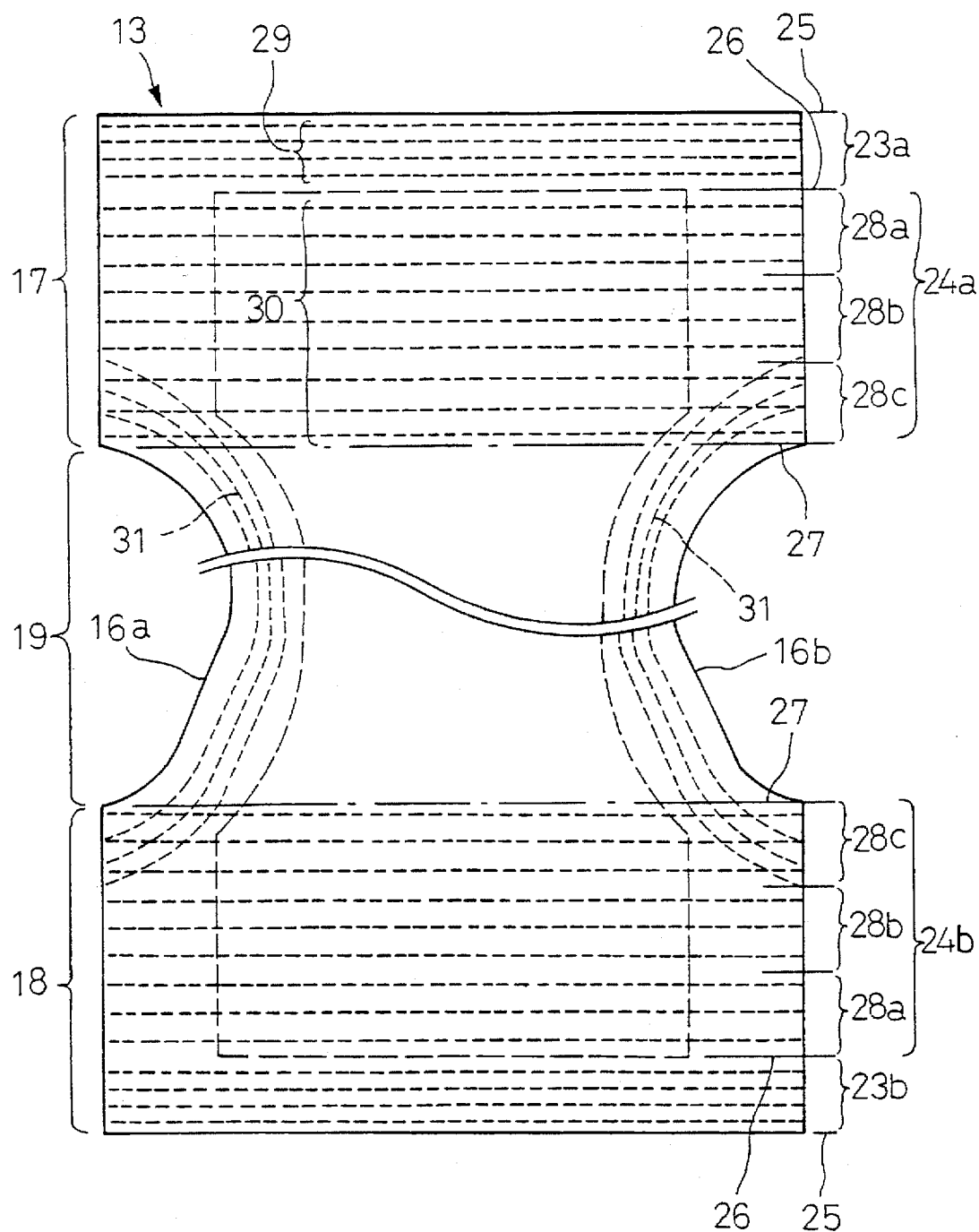
FIG. 2 is a plan view of an arrangement of elastic members in the laminated panel forming the diaper (shown unfolded)

Referring to FIGS. 1 and 2, a diaper has a rectangular laminated panel 13 comprising a liquid-permeable topsheet 10, a liquid-impermeable backsheet 11 and an hourglass-shaped liquid-absorbent core panel 12 disposed between the top- and backsheets. In the laminated panel 13, the top- and backsheets 10, 11 are bonded to each other at portions thereof extending outward beyond an outer peripheral edge of the core panel 12 so as to form longitudinally opposite end flaps 14a, 14b as well as transversely opposite side flaps 15a, 15b. The side flaps 15a, 15b have, over longitudinally middle portions thereof, cutouts 16a, 16b describing circular arcs along respective outer side edge portions of the side flaps 15a, 15b and these cutouts 16a, 16b form respective leg-openings.

The laminated panel 13 may be divided into a front waist region 17, a rear waist region 18 and a crotch region 19 extending longitudinally between the front and rear waist regions 17, 18. The laminated panel 13 is folded in two sections with the topsheet 10 inside and transversely opposite side edges 20a, 20b of the front and rear waist regions 17, 18 are intermittently ultrasonic-welded together in the longitudinal direction to obtain the desired diaper of pants type having a waist-opening 21 and a pair of leg-openings 22a, 22b.

The diaper has front and rear waist-opening marginal stretchable regions 23a, 23b as well as front and rear waist stretchable regions 24a, 24b. The front and rear waist-opening marginal stretchable regions 23a, 23b are defined between respective upper ends 25 of the waist-opening 21 and respective border lines 26 extending transversely along respective longitudinally opposite ends of the core panel 12 in the front and rear waist regions 17, 18. The front and rear waist stretchable regions 24a, 24b are defined between the respective border lines 26 and the respective border lines 27 connecting points adjacent respective upper ends of the leg-openings 22a, 22b. Each of the front and rear waist stretchable regions 24a or 24b comprises upper, intermediate and lower stretchable subregions 28a, 28b, 28c respectively dimensioned to have their widths substantially equal to ⅓ of the front or rear waist stretchable region 24a or 24b. While it is not critical for the stretchable subregions 28a, 28b, 28c to have their widths (i.e., their dimensions as selected longitudinally of the article) substantially uniform, these stretchable subregions 28a, 28b, 28c are preferably adjusted, in this order, so as to extend over an upper zone, an intermediate zone (corresponding to the prominence or apex) and a lower zone of a baby's prominent belly. Alternatively, each of the stretchable subregions 28b is preferably dimensioned to have a width larger (not shown) than both the stretchable subregions 28a, 28c so that pressure exerted on the baby's belly may be alleviated.

The front and rear waist-opening marginal stretchable regions 23a, 23b as well as the front and rear waist stretchable regions 24a, 24b have, at least on an inner surface of the backsheet 11, elastic members 29, 30 each comprising a plurality of elastic threads bonded thereon under the tension of a desired elongation percentage so as to be capable of expansion and contraction circumferentially of the front and rear waist regions 17, 18. In the specific embodiment illustrated, the front and rear waist-opening marginal stretchable regions 23a, 23b have four elastic threads or elements of member 29, respectively, and the front and rear waist stretchable regions 24a, 24b have three elastic threads or elements of member 30 on the upper, intermediate and lower stretchable subregions 28a, 28b, 28c, respectively. However, it should be understood that the number of the elastic threads or elements of members 29, 30 may be respectively at least one and preferably two to eight. If it is desired, a plurality of elastic threads or elements of member 30 may be additionally provided on areas extending below the border lines 27. Longitudinal elongation stresses presented by the elastic member 29, 30 in the front and rear waist-opening marginal stretchable regions 23a, 23b and the upper, intermediate and lower stretchable subregions 28a, 28b, 28c of the front and rear waist stretchable regions 24a, 24b are as follows:

The stretchable region 23a is approximately equal to the stretchable region 23b.

The stretchable subregion 28a of the stretchable region 24a is approximately equal to the stretchable subregion 28a of the stretchable region 24b.

The stretchable subregion 28b of the stretchable region 24a is approximately equal to the stretchable subregion 28b of the stretchable region 24b.

The stretchable subregion 28c of the stretchable region 24a is approximately equal to the stretchable subregion 28c of the stretchable region 24b.

The stretchable region 23a (or 23b) is greater than the stretchable subregion 28a or 28c of the stretchable region 24a (or 24b).

The stretchable subregion 28a or 28c of the stretchable region 24a (or 24b) is greater than the stretchable subregion 28b of the stretchable region 24a (or 24b).

The stretchable subregion 28c of the stretchable region 24a (or 24b) is greater than the stretchable subregion 28a of the stretchable region 24a (or 24b), or the stretchable subregion 28c of the stretchable region 24a (or 24b) is approximately equal to the stretchable subregion 28a of the stretchable region 24a (or 24b).

Most preferably, the stretchable region 23a (23b) is greater than the stretchable subregion 28c which is greater than the stretchable subregion 28a which is greater than the stretchable subregion 28b.

The aforesaid elongation stresses may be determined, for example, with samples of desired lengths and widths cut off the respective stretchable regions and subregions 23a, 23b, 28a, 28b, 28c of the diaper illustrated and elongated at desired elongation percentages, respectively. Of the elongation stress values determined in this manner, those values for the waist-opening marginal stretchable regions 23a, 23b are used as the basic values which are, in general, selected to be substantially equal to those in the pants type diaper. For example, assume that the elongation stresses are in a relationship such that that of the stretchable region 23a is greater than the stretchable subregion 28c, which is greater than the stretchable subregion 28a, which is greater than the stretchable subregion 28b, an arrangement will be preferable such that the elongation stress in the stretchable subregion 28c corresponds to approximately 60 to 80% of that in the stretchable region 23a, approximately 150 to 250% of that in the stretchable subregion 28a and approximately 250 to 350% of that in the stretchable subregion 28b which corresponds, in turn, to approximately 5 to 85% of that in the stretchable subregion 28a.

Such differences in the elongation stress are easily obtained by appropriately differentiating various factors such as the number, the nature of raw material, the cross-section and the elongation percentage for the respective elastic members 29, 30 when they are applied to the diaper.

Figure 3:
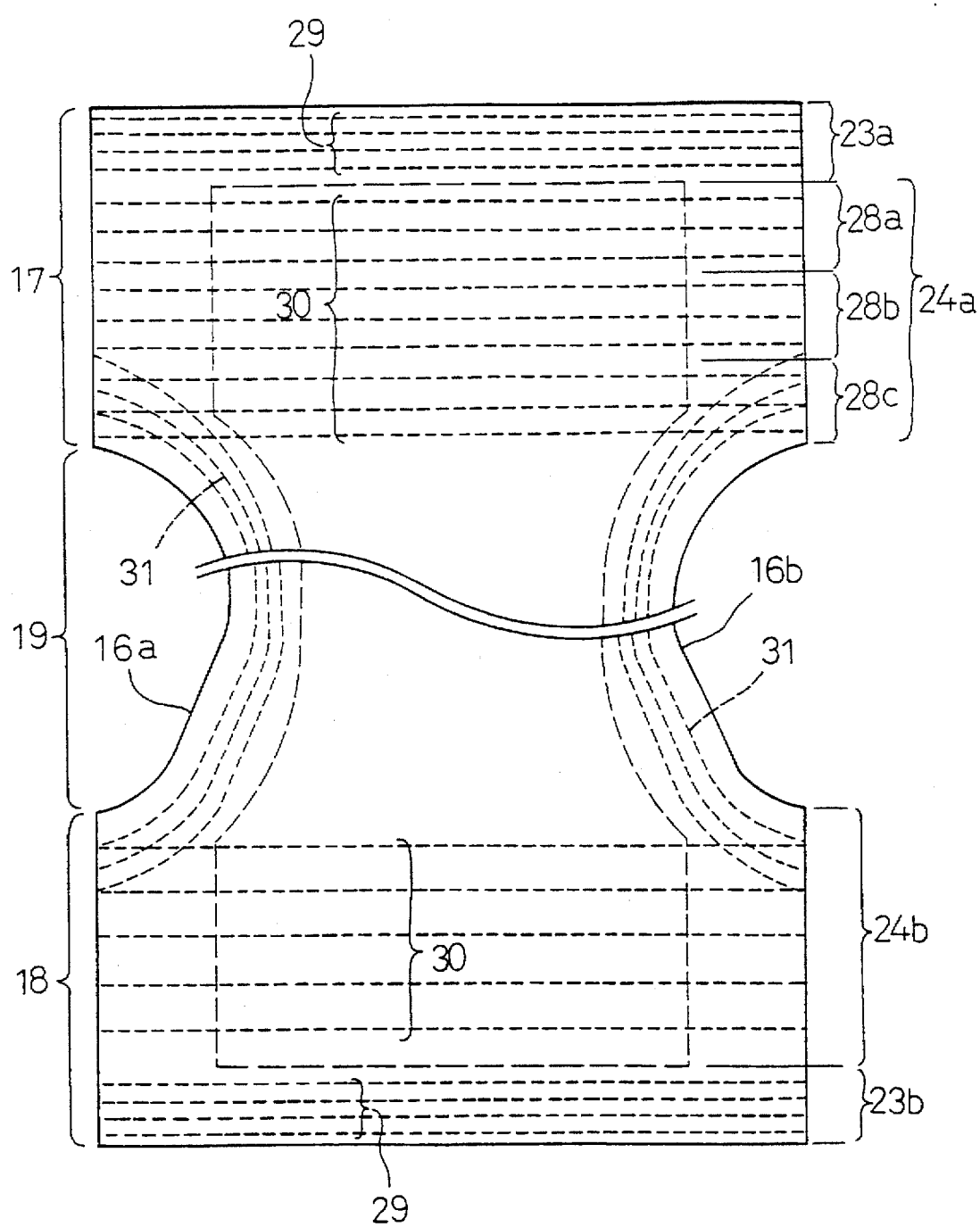
FIG. 3 is a view similar to FIG. 2, of an alternative arrangement of the elastic members.

The embodiment shown by FIG. 3 is similar to the embodiment which has been described in connection with FIGS. 1 and 2 in so far as the number, the elongation stress and the spacing for placement of the elastic elements of member 29 in the front and rear waist-opening marginal stretchable regions 23a, 23b as well as of the elastic elements of member 30 in the front waist stretchable region 24a are concerned, but is different from the embodiment of FIGS. 1 and 2 with respect to the number, the elongation stress and the spacing for placement of the elastic elements of member 30 in the rear waist stretchable region 24b. More specifically, the elongation stress of the elastic member 30 in the rear waist stretchable region 24b is adjusted to be uniform over all but less than in the stretchable subregion 28c of the front waist stretchable region 24a.

The leg-openings 22a, 22b or the cutouts 16a, 16b to form the respective leg-openings 22a, 22b have, at least on an inner surface of the backsheet 11, elastic members 31 each comprising a plurality of elastic threads bonded thereto under the tension of a desired elongation percentage circumferentially of the leg-openings 22a, 22b or along the curves of the cutouts 16a, 16b, respectively.

The waist-opening marginal stretchable regions 23a, 23b and the upper stretchable subregion 28a of the front waist stretchable region 24a extend over the upper region of a baby's belly so as to hold an inner surface of the diaper against this region with a relatively high tightness and thereby prevent "slip down" of the diaper. The upper stretchable subregion 28a additionally serves to prevent a region of the diaper extending in the proximity of the upper end of the core panel 12 from being lifted off a baby's skin due to a relatively high rigidity of the panel 12. The intermediate stretchable subregion 28b of the front waist stretchable region 24a extends over a region of a baby's belly in the proximity of its prominence apex and is brought in relatively soft contact with this region to prevent the inner surface of the diaper on this region from being lifted off from a baby's skin without obstructing the baby's smooth abdominal breathing. The lower stretchable subregion 28c of the front waist stretchable region 24a extends over a lower region of a baby's belly not only to hold the inner surface of the diaper against this region with a relatively high tightness and thereby to prevent "slip down" of the diaper but also to avoid an apprehension that the inner surface of the diaper in the proximity of the upper ends of the respective leg-openings 22a, 22b might be lifted off a baby's skin due to a relatively high rigidity of the core panel 12 whereby a gap might be formed between the inner surface of the diaper and a baby's skin which causes excretion leakage. While the aforesaid function of the front waist stretchable region 24a is really achieved in cooperation with the rear waist stretchable region 24b, it should be understood that the function of the front waist stretchable region 24a has been considered independently of the rear waist stretchable region 24b, since, in view of a baby's particular body form, much importance should be attached to the front waist stretchable region 24a rather than the rear waist stretchable region 24b in order to solve the problems of "slip down" and excretion leakage.

The elastic members 29, 30 are bonded between the top- and backsheets 10, 11 by means of well known hot melt adhesive and, more preferably, by means of such adhesive having an elasticity in its cured state. While opposite ends of the elastic members 30 in the stretchable subregions 28c intersect opposite ends of the elastic members 31 according to the embodiments illustrated, it is obviously possible to arrange the elastic members 30, 31 without intersecting in this manner. However, the elastic members 30, 31 are preferably arranged so that said intersection occurs, since the elastic members 30 have a relatively high density in the regions involving such intersection and contributes to improvement of the diaper's fitness to a baby's skin.

Figure 4:
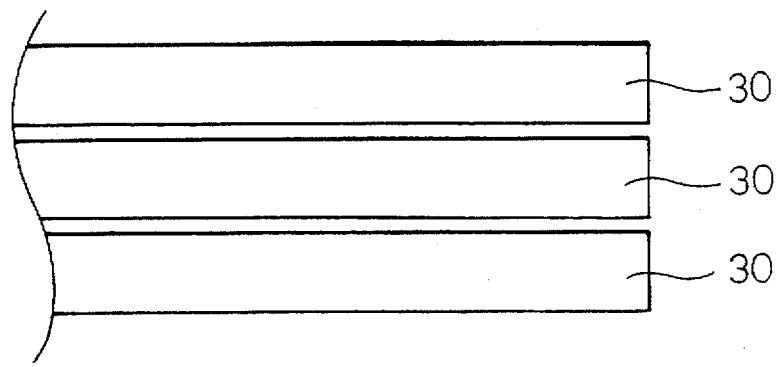
FIG. 4 is a fragmentary plan view showing another type of the elastic members.
Figure 5:
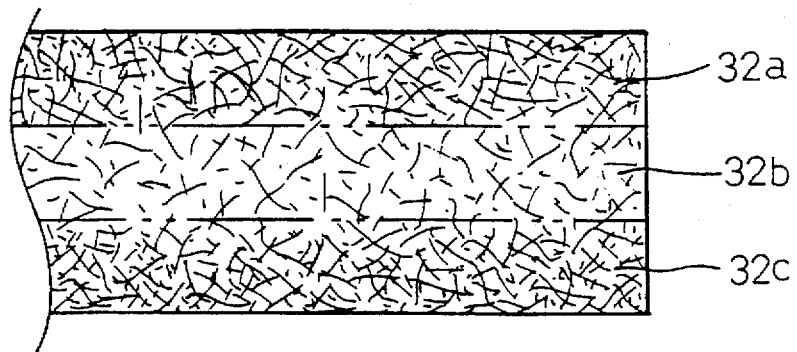
FIG. 5 is a view similar to FIG. 4, showing still another type of the elastic members.

According to an alternative arrangement of the elastic member 30 shown by FIG. 4, the elastic threads are replaced by tape-like elastic elements and each of the stretchable subregions 28a, 28b, 28c has a single tape-like elastic element. Alternatively, the stretchable subregions 28a, 28b, 28c may be formed by a single sheet having subregions 32a, 32b, 32c presenting elongation stresses corresponding to those of the aforesaid stretchable subregions 28a, 28b, 28c. Such a sheet can be obtained by regulating an amount of discharged fibers so that the subregions 32b which should have a relatively low elongation stress may be formed with a weight per unit area less than those of the other subregions during a process of manufacturing an elastic melt blown nonwoven fabric.

Well known materials which have conventionally been employed to make a pants type diaper may be employed for the components of the invention such as the top- and backsheets 10, 11, the core panel 12, and the elastic members 29, 30, 31.

The article according to the invention not only does not obstruct a baby's smooth abdominal breathing but also effectively prevents the aforesaid "slip down" of the article and therefore excretion leakage during use of the article, since, in view of a prominent belly and the abdominal breathing characterizing babies, the elastic members are arranged in the front and rear waist stretchable regions in the manner as described in claims.

What is claimed is:

1. An absorbent pants type article, comprising a laminated panel including a liquid-permeable topsheet, a liquid-impermeable backsheet and a liquid absorbent core panel disposed between said topsheet and said backsheet, said laminated panel having a transverse direction and a longitudinal direction, said laminated panel being folded in two sections which are bonded together along transversely opposite side edges thereof except along longitudinally intermediate regions so as to define front and rear waist regions, a crotch region, a waist-opening and a pair of leg-openings; a first elastic member extending around said waist-opening so as to be circumferentially stretchable, a second elastic member extending around each of said leg-openings so as to be circumferentially stretchable and a third elastic member located between said waist-opening and said leg-openings and extending transversely across said core panel so as to be circumferentially stretchable;

said first elastic member being arranged in front and rear waist-opening marginal stretchable regions defined between respective portions of an upper end of said waist-opening and respective first border lines extending transversely along respective upper ends of said core panel in said front and rear waist regions;

said third elastic member being provided on said front waist region in a front waist stretchable region defined between said first border line in said front waist region and a second border line in said front waist region connecting respective upper portions of said pair of leg-openings;

said front waist stretchable region comprises upper, intermediate and lower stretchable subregions and said third elastic member provided in each of said subregions; and said first elastic member in said front waist-opening marginal stretchable region has an elongation stress higher than an elongation stress of said third elastic member in each of said upper and lower stretchable subregions and said third elastic member in said upper and lower stretchable subregions has an elongation stress higher than an elongation stress of said third elastic member in said intermediate stretchable subregion.

2. The article according to claim 1, wherein said third elastic member in said lower stretchable subregion has an elongation stress higher than the elongation stress of said third elastic member in said upper stretchable subregion.

3. The article according to claim 1, wherein said third elastic member in said lower stretchable subregion has an elongation stress substantially equal to the elongation stress of said third elastic member in said upper stretchable subregion.

4. The article according to claim 1, wherein said third elastic member is also provided in said rear waist region and is in a rear waist stretchable region defined between said first border line in said rear waist region and a second border line in said rear waist region connecting respective upper portions of said pair of leg-openings;

said rear waist stretchable region comprises upper, intermediate and lower stretchable subregions and said third elastic member provided in each of said subregions of said rear waist stretchable region;

said first elastic member in said rear waist-opening marginal stretchable region has an elongation stress substantially equal to the elongation stress of said first elastic member in said front waist-opening marginal stretchable region but higher than an elongation stress of said third elastic member in each of said upper and lower stretchable subregions of said rear waist stretchable region;

said third elastic member in each of said upper and lower stretchable subregions of said rear waist stretchable region has an elongation stress substantially equal to the elongation stress of said third elastic member in each of said upper and lower stretchable subregions of said front waist stretchable region but higher than an elongation stress of said third elastic member in said intermediate stretchable subregion of said rear waist stretchable region; and said third elastic member in said intermediate stretchable subregion of said rear waist stretchable region an an elongation stress substantially equal to the elongation stress of said third elastic member in said intermediate stretchable subregion of said front waist stretchable region.

5. The article according to claim 4, wherein said third elastic member in said lower stretchable subregion of said rear waist stretchable region has an elongation stress higher than the elongation stress of said third elastic member in said upper stretchable subregion of said rear waist stretchable region.

6. The article according to claim 4, wherein said third elastic member in said lower stretchable subregion of said rear waist stretchable region has an elongation stress substantially equal to the elongation stress of said third elastic member in said upper stretchable subregion of said rear waist stretchable region.

7. The article according to claim 4, wherein a number of elastic elements forming said third elastic member in said rear waist stretchable region is less than an number of elastic elements forming said third elastic member in said front waist stretchable region.

8. The article according to claim 4, wherein said third elastic member in said upper, intermediate and lower stretchable subregions of said rear waist stretchable region is formed by a single sheet.

9. The article according to claim 1, wherein said third elastic member is also provided in said rear waist region and is in a rear waist stretchable region defined between said first border line in said rear waist region and a second border line in said rear waist region connecting respective upper portions of said pair of leg-openings;

said first elastic member in said rear waist-opening marginal stretchable region has an elongation stress substantially equal to the elongation stress of said first elastic member in said front waist-opening marginal stretchable region but higher than an elongation stress of said third elastic member in said rear waist stretchable region;

said third elastic member in said rear body stretchable region has an elongation stress which is substantially uniform over all said rear waist stretchable region but less than the elongation stress of said third elastic member in said lower stretchable subregion of said front waist stretchable region.

10. The article according to claim 1, wherein each of said upper, intermediate and lower stretchable subregions of said front waist stretchable region comprises at least a single elastic element as said third elastic member.

11. The article according to claim 1, wherein said third elastic member in said upper, intermediate and lower stretchable subregions of said front waist stretchable region is formed by a single sheet.

* * * * *